Figure 1:
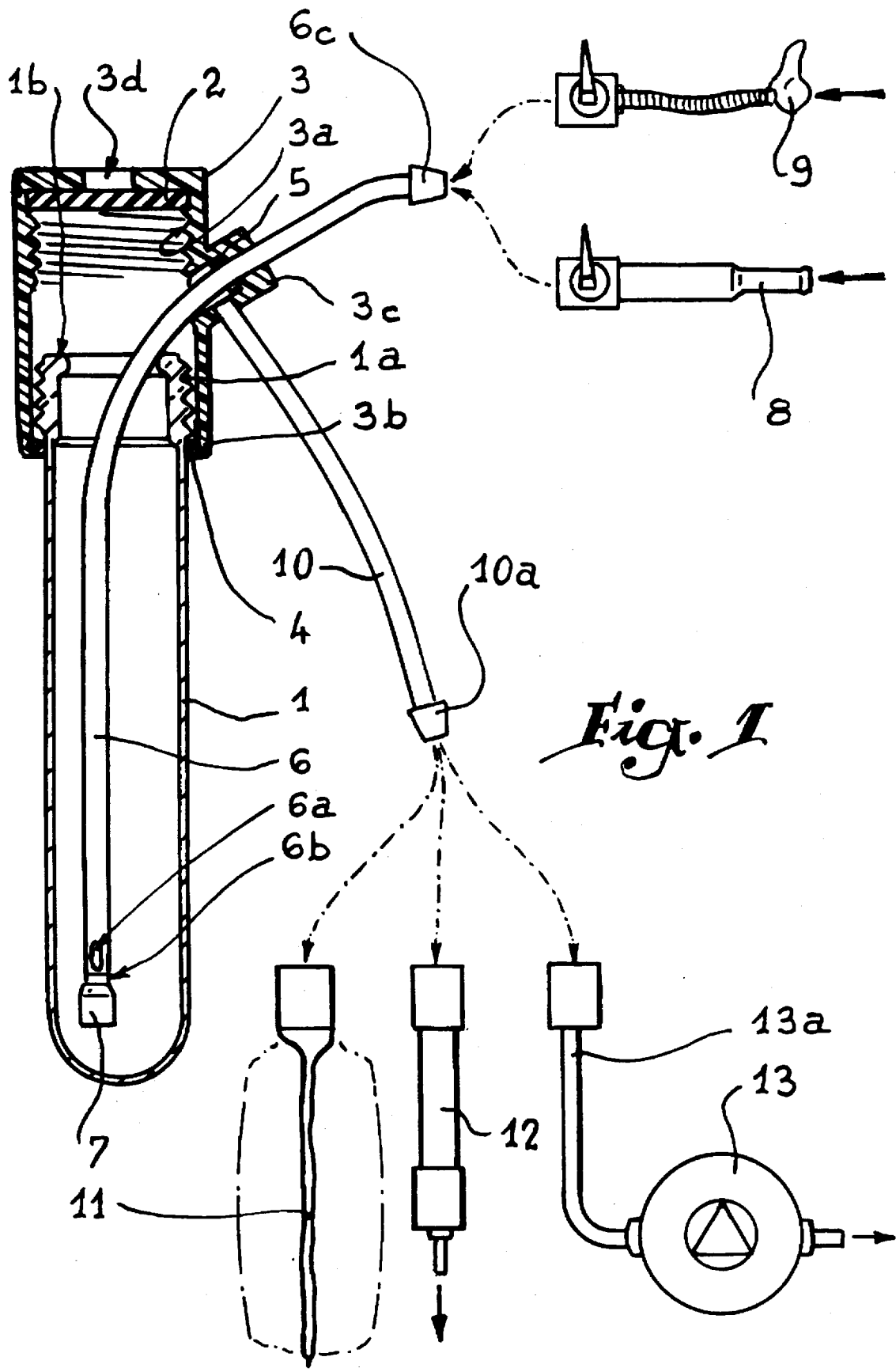

United States Patent [19]

Guilluy

[11] Patent Number: 5,711,306
[45] Date of Patent: Jan. 27, 1998

[54] ONE-USE DEVICE FOR DIRECTLY TAKING A SAMPLE OF EXPIRED AIR FROM A SUBJECT

[75] Inventor: Roger Guilluy, Saint Bonnet de Mure, France

[73] Assignee: INBIOMED International, Lyons, France

[21] Appl. No.: 704,520
[22] PCT Filed: Mar. 21, 1995
[86] PCT No.: PCT/FR95/00346
§ 371 Date: Sep. 4, 1996
§ 102(e) Date: Sep. 4, 1996
[87] PCT Pub. No.: WO95/25462
PCT Pub. Date: Sep. 28, 1995

[30] Foreign Application Priority Data

Mar. 22, 1994 [FR] France .................. 94 03618

[51] Int. Cl.⁶ .................. G01N 33/00; A61R 5/08
[52] U.S. Cl. .......... 128/730; 215/228; 215/247; 215/248; 215/43; 215/45; 215/307
[58] Field of Search .................. 128/716, 719, 128/727–730; 215/247, 248, 228, 229, 43, 45, 307

[56] References Cited

U.S. PATENT DOCUMENTS

| | | | |
|---|---|---|---|
| 2,241,097 | 5/1941 | Mezzapesa | 215/247 |
| 3,419,172 | 12/1968 | Lee | 215/45 |
| 4,204,606 | 5/1980 | Micheli | |
| 4,355,111 | 10/1982 | Shimizu et al. | 215/307 |
| 4,821,895 | 4/1989 | Roskilly | 215/228 |
| 5,024,663 | 6/1991 | Yum | |
| 5,211,181 | 5/1993 | Delente | 128/730 |
| 5,432,094 | 7/1995 | Delente | 128/730 |
| 5,525,299 | 6/1996 | Lowe | 215/228 |

FOREIGN PATENT DOCUMENTS

| | | |
|---|---|---|
| 8101238 | 5/1981 | WIPO . |
| 9220278 | 11/1992 | WIPO . |

*Primary Examiner*—Jennifer Bahr
*Assistant Examiner*—Stephen Huang
*Attorney, Agent, or Firm*—Dowell & Dowell

[57] ABSTRACT

An apparatus to directly take a sample of expired air from a subject which utilizes a stopper (3) with two distinct position. When the stopper (3) is in the upper position, it allows air blown in via the cannula (6) to scavenge the interior space of the tube (1) until the control (11,12, or 13) has indicated a sufficient volume. The cannula (6) is then pulled by the operator so that a blind stop (7) obturates the opening of an evacuation pipe (10) connected to the control. The stopper is then moved to a lower position to seal the sample of air in the tube (1).

8 Claims, 2 Drawing Sheets

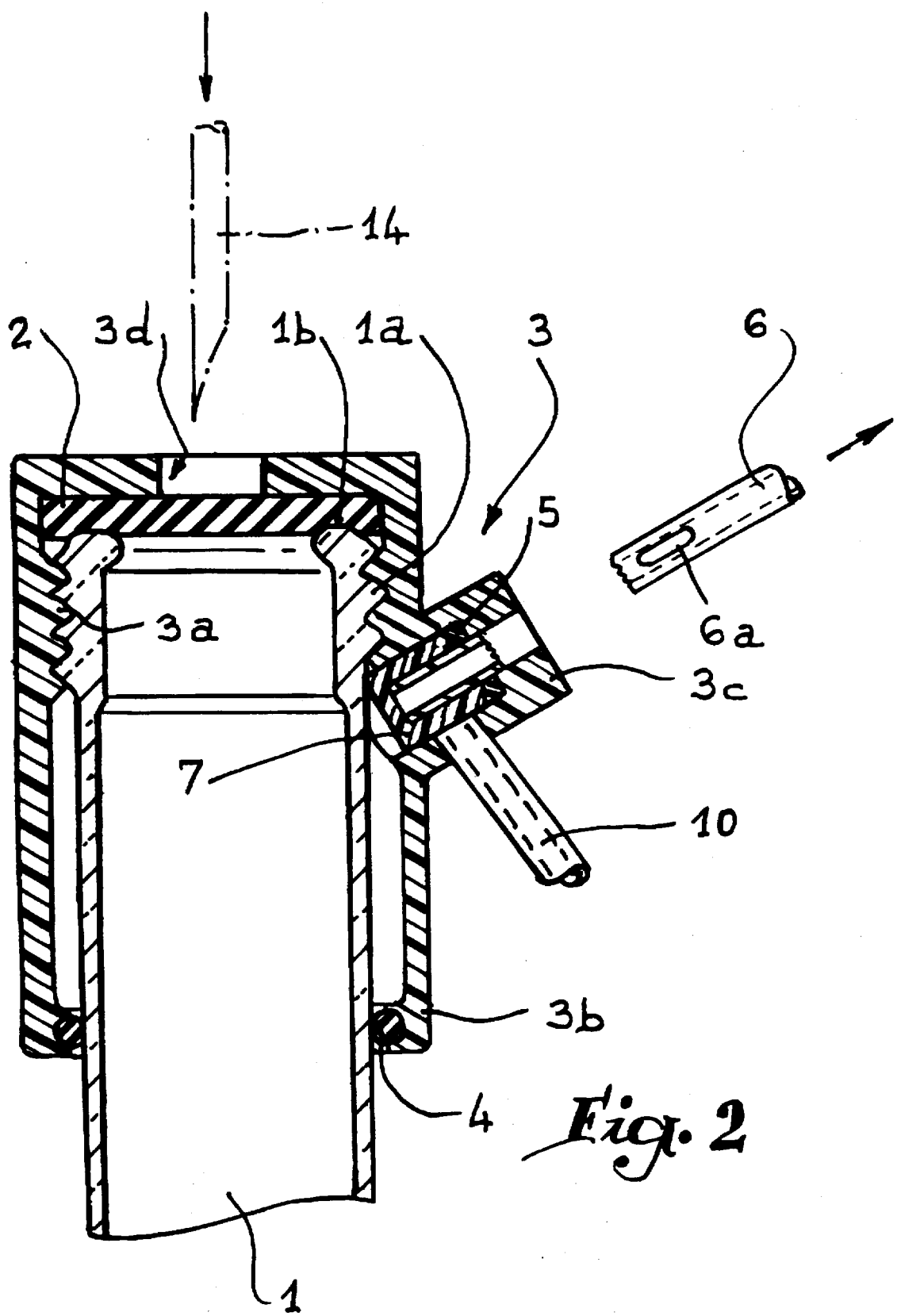

ONE-USE DEVICE FOR DIRECTLY TAKING A SAMPLE OF EXPIRED AIR FROM A SUBJECT

The present invention relates to a one-use device which enables a sample of expired air to be taken directly from a subject with a view to subsequent analysis in the laboratory, and more particularly an isotopic analysis of the $^{13}CO_2$ within the framework of the so-called "Breath Test" method.

It is known that the variation of the isotopic enrichment with carbon 13 of the carbon dioxide ($CO_2$) contained in the air expired by a subject, after administration to the latter of a specific substrate enriched with $^{13}C$, enables clinical investigations for final diagnosis to be made. In fact, the measurement bears on very slight variations, with the result that the mode of taking the gaseous samples and the material used to that end are of primordial importance, making it impossible to employ the systems of sampling by multilayer plastic bags usually used for taking samples of gas in the atmosphere.

In practice, glass tubes, pre-packed in vacuo, are generally employed, which are normally used for taking blood samples, but experiments carried out show that this type of recipient is not suitable for obtaining reliable samples of expired air. Manipulations are complex since the subject must blow in and fill an air-tight bag, from which a volume of air must be transferred immediately in the tube. Filling of the tube depends on the level of vacuum prevailing inside it, which level can never be guaranteed.

It is a principal object of the present invention to overcome these drawbacks, with the aid of the special sampling device forming the subject matter thereof.

This device comprises, in combination:

a rigid recipient, advantageously constituted by a conventional glass tube, whose volume corresponds to that desired of the sample to be taken;

a stopper adapted to take two axial positions on the recipient; ensuring obturation of the upper, open part thereof; which stopper is fast with a lateral tube whose inner opening is obturated by the wall of the recipient when said stopper has been brought to the lower axial position of seal;

a cannula engaged to slide axially in the lateral tube, the subject blowing into one of the ends of this cannula, while the opposite end which opens freely in the recipient is provided with a blind, annular, projecting stop;

an evacuation pipe of which the opening in the lateral tube is obturated by the blind annular stop of the cannula once the latter has been displaced axially by the operator pulling;

and a control volume which is connected to the free end of the evacuation pipe and which is arranged to indicate to the operator that a sufficient volume of expired air has passed through and scavenged the recipient.

The accompanying drawings, given by way of example, will enable the invention, the characteristics that it presents and the advantages that it is capable of procuring, to be more readily understood.

FIG. 1 is an axial section illustrating the general arrangement of a sampling device according to the invention.

FIG. 2 partially reproduces on a larger scale the section of FIG. 1, after the stopper has been lowered and the insufflation cannula pulled out.

The sampling device illustrated firstly comprises a rigid recipient formed by a glass tube 1 of conventional type, of which the open upper part comprises a threading 1a, while the top wall 1b is provided to be plane in order to cooperate with a perforatable membrane 2.

With this tube 1 there is associated a stopper 3 whose cylindrical skirt presents an upper threading 3a adapted to cooperate with threading 1a; the bottom of this skirt is profiled at 3b to hold an O-ring 4, thus applied tightly against the outer wall of the tube 1.

It should be observed that the skirt of the stopper 3 is fast with a lateral tube 3c oriented obliquely upwardly. The axial bore of this tube 3c presents two diameters so as to define an annular shoulder which holds an O-ring 5, whose function will be seen hereinbelow, in place.

In tube 3c there is engaged to slide axially a cannula 6 which, in the immediate vicinity of its lower end enclosed in the tube 1, is pierced laterally with at least one slot 6a for communication. Therebelow, the cannula 6 is equipped with a blind annular stop 7 which thus defines a projecting part; between the stop 7 and the slot 6a there is provided an annular incipient break 6b.

The free upper end of the cannula 6 is provided with a cone 6c allowing it to be connected to an insufflation apparatus which may be constituted either by a mouthpiece 8 or by a mask such as the one indicated at 9. Mouthpiece 8 and mask 9 are advantageously equipped with an interception member such as a cock or a diaphragm valve.

The sampling device further comprises an evacuation pipe 10 of which one end is engaged in a hole made transversely in the lateral tube 3c of the stopper 3. The opposite end is provided with a cone 10a with a view to its selective connection either to a not elastically expansible, inflatable balloon 11, to a control tube 12 containing a reagent, or to the admission 13a of a micro-pump 13 whose drive motor is supplied to suck a determined volume of air.

The device is normally delivered with the stopper 3 in the upper position for filling, illustrated in FIG. 1. Using the mouthpiece 8 or mask 9, possibly with the assistance of the micro-pump 13, the subject blows into the cannula 6 a quantity of air sufficient either to fill the balloon 11, or to alter the reagent contained in the control tube 12. It is thus sure that the interior space of the tube 1 has been completely rinsed by a scavenging of expired air.

Once this result is obtained, the operator pulls sharply on the cannula 6 in order to slide it in the tube 3c until the terminal stop 7 is in abutment against the O-ring 5 and said cannula is cut at the level of the incipient break 6b (cf. FIG. 2). At that moment, the pipe 10 can be removed without the outer air being able to penetrate in the tube 1, as the hole which held the end of this pipe 10 is tightly obturated by the stop 7 in abutment against the O-ring 5.

The operator therefore has the necessary time to manoeuvre the stopper 3 axially then in rotation, and it is thus brought to the lower position of seal illustrated in FIG. 2, for which the membrane 2 is firmly applied against the top face 1b of the tube 1 thus closed reliably and definitively. This tube 1, filled with a sample of perfectly determined volume, may easily be sent to a laboratory for analysis. This sample of air may be removed from the tube 1 with the aid of a syringe whose trocar 14 is introduced through a central opening 3d in the upper end of the stopper 3 to perforate the membrane 2.

The device is, of course, to be used once only, this contributing to guaranteeing the authenticity of the sample taken. The immediate isolation of the sample inside the tube 1 avoids any risk of outside contamination. Manipulations are simple since no decantation is required and no particular skill is required of the operators. The tube 1 may take the shape of any recipient.

It must, moreover, be understood that the foregoing description has been given only by way of example and that it in no way limits the domain of the invention which would not be exceeded by replacing the details of execution described by any other equivalents.

I claim:

1. One-use device for directly taking a sample of expired air from a subject, comprising, in combination:

a rigid recipient (1), whose volume corresponds to that desired of the sample to be taken;

a stopper (3) adapted to take two axial positions on the recipient (1), ensuring obturation of an upper, open part thereof in one or the other of the two positions, which stopper is fast with a lateral tube (3c) whose inner opening is obturated by a wall of the recipient when said stopper has been brought to a lower axial position of seal;

a cannula (6) engaged to slide axially in the lateral tube (3c), the subject blowing into one of the ends of this cannula, while an opposite end which opens freely in the recipient (1) is provided with a blind, annular, projecting stop (7);

an evacuation pipe (10) of which the opening in the lateral tube (3c) is obturated by the blind annular stop (7) of the cannula (6) once the cannula has been displaced axially by an operator pulling;

and a control volume (11, 12, 13) which is connected to the free end of the evacuation pipe (10) and which is arranged to indicate to the operator that a sufficient volume of expired air has passed through and scavenged the recipient (1).

2. Device according to claim 1, characterized in that the recipient comprises by a glass tube (1) whose open upper part presents a threading (1a) to cooperate with a corresponding threading (3a) of the stopper (3).

3. Device according to claim 2, characterized in that, below the threading (3a), a skirt of the stopper (3) is shaped (at 3b) to retain an O-ring (4) applied tightly against an outer wall of the tube (1).

4. Device according to claim 1, characterized in that there is associated with the stopper (3) a membrane (2) adapted to be applied tightly against a top face of the stopper (1b), provided to be plane to that end, of the recipient (1), a bottom of said stopper comprising a central opening (3d) for passage of trocar (14) of a syringe intended, after piercing said membrane, to remove the sample of air enclosed in said recipient.

5. Device according to claim 1, characterized in that the lateral tube (3c) comprises an oxial bore which presents two diameters so as to define an annular shoulder ensuring hold of an O-ring (5), which forms abutment for the blind stop (7).

6. Device according to claim 1, characterized in that, immediately above the stop (7), an insufflation cannula (6) presents an incipient break (6b) which is disposed below the lateral slot (6a) constituting an opening of said cannula in the recipient (1).

7. Device according to claim 1, characterized in that an outer end of the cannula (6) is equipped with a cone (6c) for connection with an oral insufflation apparatus such as a mouthpiece (8) or a mask (9).

8. Device according to claim 1, characterized in that the free end of the evacuation pipe (10) is equipped with a cone (10a) for selective connection to the control volume which may be constituted by either, an inflatable balloon (11), a tube (12) containing a reagent, or a micro-pump (13) with controlled flowrate.

* * * * *